United States Patent [19]

Cole et al.

[11] Patent Number: 4,957,733
[45] Date of Patent: Sep. 18, 1990

[54] PHARMACEUTICAL PRODUCTS

[75] Inventors: Martin Cole, Betchworth; Malcolm R. Boyd; David Sutton, both of Epsom, all of England

[73] Assignee: Beecham Group P.L.C., England

[21] Appl. No.: 126,406

[22] Filed: Nov. 30, 1987

[30] Foreign Application Priority Data

Dec. 2, 1986 [GB] United Kingdom ............... 8628826

[51] Int. Cl.$^5$ ............................................. A61K 37/66
[52] U.S. Cl. .................................. 424/85.4; 424/85.5; 424/85.6; 424/85.7
[58] Field of Search ................. 424/85.4, 85.5, 85.6, 424/85.7

[56] References Cited

U.S. PATENT DOCUMENTS 4,461,757 7/1984 Ogilvie .................................. 424/85
4,606,917 8/1986 Eppstein ............................... 424/85

FOREIGN PATENT DOCUMENTS 0182024 5/1986 European Pat. Off. .

OTHER PUBLICATIONS

Chemical Abstracts, vol. 101, Abstract No. 257t, 1984.

Spector et al., Antimicrobial Agents and Chemotherapy, vol, 23, pp. 113–118, 1983.
Bryson et al., Antimicrobial Agents and Chemotherapy, vol. 11, pp. 299–306, 1977.
Ikic et al., International Journal of Clinical Pharmacology, Therapy and Toxicology, vol. 19, No. 11, 1981, pp. 488–504.

*Primary Examiner*—Blondel Hazel
*Attorney, Agent, or Firm*—Hopgood, Calimafde, Kalil, Blaustein & Judlowe

[57] ABSTRACT

Pharmaceutical product comprising an interferon and a compound of formula (A)

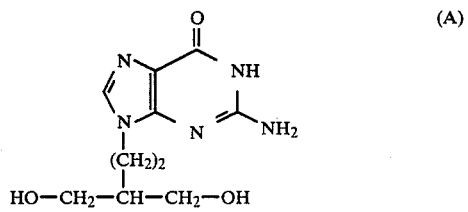

or a pro-drug, or a pharmaceutically acceptable salt, phosphate ester and/or acyl derivative or either of the foregoing as a combined preparation for simultaneous, separate or sequential use in antiviral therapy.

7 Claims, No Drawings

PHARMACEUTICAL PRODUCTS

The present invention relates to pharmaceutical products having antiviral activity.

EP-A-No. 141927 discloses the compounds of formula (A):

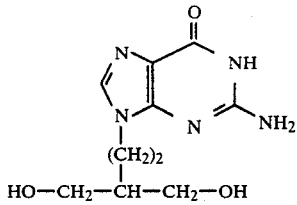

and salts, phosphate esters and acyl derivatives thereof, as antiviral agents.

Pro-drugs of the compound of formula (A) are of formula (B):

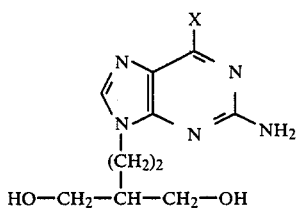

and salts and derivatives thereof as defined under formula (A); wherein X is $C_{1-6}$ alkoxy, $NH_2$ or hydrogen. The compounds of formula (B) wherein X is $C_{1-6}$ alkoxy or $NH_2$ are disclosed in EP-A-No.141927 and the compound of formula (B) wherein X is hydrogen are disclosed in EP-A-No. 182024. A particularly preferred example of a compound of formula (B) is that wherein X is hydrogen and wherein the two OH groups are in the form of acetyl derivatives, described in Example 2 of EP-A-No. 182024.

Interferons are proteins produced by various types of mammalian cells or by genetic engineering methods. Their properties, chemical nature and methods of preparation and recovery have been extensively studied and documented in recent years, because of their potentially valuable therapeutic properties, (ref. E. Knight Jr., 'Purification and characterisation of Interferons' in Interferon 2, 1980 ed. I. Gressor Academic Press, London; and Antiviral Research, 6 (1986) 1-17.

It has now been found that a combination of an interferon and a compound of formula (A) or a pro-drug or a pharmaceutically acceptable salt and/or derivative as defined, of either of the foregoing has good antiviral activity. The effectiveness of the combination is greater than could be predicted from a consideration of the antiviral activities of the individual components and it appears that a synergistic effect is being produced.

Accordingly, the present invention provides a pharmaceutical product comprising an interferon and a compound of formula (A)

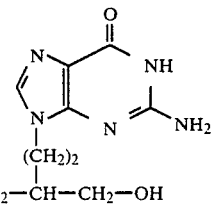

or a pro-drug, or a pharmaceutically acceptable salt, phosphate ester and/or acyl derivative of either of the foregoing as a combined preparation for simultaneous, separate or sequential use in antiviral therapy.

In a preferred aspect, the active components of the product are administered simultaneously.

The present invention further provides a pharmaceutical composition comprising an interferon and a compound of formula (A) or a pro-drug, salt and/or derivative thereof, in combination with a pharmaceutically acceptable carrier.

The invention yet further provides the use of interferon and a compound of formula (A) or a pro-drug, or a salt and/or derivative thereof as defined, in the manufacture of a combined preparation for simultaneous, separate or sequential use in antiviral therapy.

The term 'acyl derivative' is used herein to include any derivative of the compounds of formula (A) in which one or more acyl groups are present. Such derivatives are included as pro-drugs of the compounds of formula (A) in addition to those derivatives which are per se biologically active.

Examples of pro-drugs, pharmaceutically acceptable salts and derivatives are as described in the aforementioned European Patent references, the subject matter of which are incorporated herein by reference. The compound of formula (A) may also be in one of the forms disclosed in EP-A-No. 216459.

Interferon is known to exist in several types ($\alpha$, $\beta$ and $\gamma$). Any type of interferon may be useful in the product and composition of the present invention. Interferon concentrations are commonly expressed as standard "units" which are internationally accepted and documented, and relate to the potency of a given quantity of interferon to inhibit a virus replication under standard conditions.

The interferon is preferably prepared synthetically, for example by genetic engineering methods, and is in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%.

The above described products and compositions have antiviral activity, and are potentially useful in the treatment of infections caused by herpes viruses, such as herpes simplex type 1, herpes simplex type 2, varicella zoster viruses, Epstein-Barr virus and cytomegalovirus.

The compounds of formula (A), pro-drugs, salts and derivatives may be prepared as described in the aforementioned European Patent references.

The product of the invention may be administered by the oral route to humans and may be compounded in the form of syrup, tablets or capsule for either separate, sequential or simultaneous administration. When the product or either active component thereof is in the form of a tablet, any pharmaceutical carrier suitable for formulating such solid compositions may be used, for example magnesium stearate, starch, lactose, glucose, rice, flour and chalk. The product or either active component thereof may also be in the form of an ingestible capsule, for example of gelatin, to contain the compound(s), or in the form of a syrup, a solution or a suspension. Suitable liquid pharmaceutical carriers include ethyl alcohol, glycerine, saline and water to which flavouring or colouring agents may be added to form syrups.

For parenteral administration, fluid unit dose forms are prepared containing a product of the present invention or an active component thereof and a sterile vehicle. The product or component, depending on the vehicle and the concentration, can be either suspended or dissolved. Parenteral solutions are normally prepared by dissolving the product or component thereof in a vehicle and filter sterilising before filling into a suitable vial or ampoule and sealing. Advantageously, adjuvants such as a local anaesthetic, preservatives and buffering agents are also dissolved in the vehicle. To enhance the stability, the composition (separate components, or mixed) can be frozen after filling into the vial and the water removed under vacuum.

Parenteral suspensions are prepared in substantially the same manner except that the product or component thereof is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

Preferred parenteral formulations include aqueous formulations using sterile water or normal saline, at a pH of around 7.4.

As is common practice, the compositions will usually be accompanied by written or printed directions for use in the medical treatment concerned.

The composition may also be formulated for topical application to the skin or eyes. For topical application to the skin, the composition may be in the form of a cream, lotion or ointment. These formulations may be conventional formulations well known in the art, for example, as described in standard books of pharmaceutics and cosmetics, such as Harry's Cosmeticology published by Leonard Hill Books and the British Pharmacopaeia. A particularly advantageous formulation for topical application to the skin, incorporates a detergent, sodium lauryl sulphate as an additional ingredient. The composition for application to the eyes may be a conventional eye-drop composition well known in the art, or an additional ointment composition.

The amount of interferon, as noted above, is commonly expressed in standard units. Generally, compositions containing from about 50–500,000 units interferon per milligram of the compound of formula (A) or a pro-drug, or a salt, phosphate ester, acyl derivative or pro-drug thereof are effective. Preferred compositions are those containing from about 1,000–200,000 units of interferon per milligram of the compound of formula (A) or a pro-drug, or a salt, phosphate ester, acyl derivative thereof.

Preferably, the product of this invention is in unit dosage form or in some other form that may be administered in a single dose. A suitable dosage unit might contain from 50 mg to 1 g of total active ingredients, for example 100 to 500 mg. Such doses may be administered 1 to 4 times a day or more usually 2 or 3 times a day. The effective dose of compound will in general be in the range of from 0.2 to 40 mg of total drugs per kilogram of body weight per day or more usually 10 to 20 mg/kg per day.

It is preferred to treat the infection with relatively large doses of the combination product at the outset, so as to limit the chances of development of resistant viral strains in the infection.

For topical administration, ointments or creams in conventional inert bases (e.g. petrolatum, etc) can be formulated, in the known way. An amount from about 0.10–10 weight per cent of total drugs, preferably from about 0.5–5 weight per cent of total drugs, provides a suitable concentration in an ointment or cream, for topical administration 1–4 times per day. Such topically applied formulations are effectively holding a reservoir of the active drugs against the infected site, so that the concentrations of drugs in the formulations are not critical, provided of course that a dosage level harmful to surrounding skin areas is not used.

It will further be appreciated that each component of the product of the invention may be administered by a different route. For example, the compound of formula (A) or a pro-drug by the oral route and interferon by an intramuscular route.

The invention also provides a method of treating viral infections in a human or non-human animal, which comprises administering to the animal an effective, non-toxic amount of a combination of an interferon and a compound of formula (A) or a pro-drug thereof, or a pharmaceutically acceptable salt, phosphate ester, acyl derivative of either of the foregoing.

The present invention further provides a method of treating viral infections in human and non-human animal which comprises administering to the animal an anti-virally effective non-toxic amount of a pharmaceutical composition comprising an interferon and a compound of formula (A) or a pro-drug thereof, or a pharmaceutically acceptable salt, phosphate ester, acyl derivative of either of the foregoing, in combination with a pharmaceutically acceptable carrier.

The effectiveness of the combination of the invention is illustrated by the following biological test data.

BIOLOGICAL TEST DATA

Test for synergy between the compound of formula (A) and human interferon against Herpes Simplex Virus Types 1 and 2 in plaque reduction assays in MRC-5 cells.

MRC-5 cells were grown to confluence in 24 well multidishes (well diameter—1.5 cm). The drained cell monolayers were each infected with approximately 50–100 infectious particles of herpes simplex virus 1 or 2 (HSV-1, strain SC16; HSV-2, strain MS) in 100 $\mu$l of phosphate-buffered saline. The virus was adsorbed for 1 hour at room temperature. After adsorption, residual inoculum was removed from each well and replaced with 0.5 ml of Eagle's MEM containing 5% newborn calf serum and 0.9% agarose (A37). Once the agarose had set, dilutions of the test compounds, which had been prepared in Eagle's MEM (containing 5% newborn calf serum), were added, each well receiving 0.25 ml of each component i.e. a total of 0.5 ml. The compound of Formula (A) was diluted to give the following series of concentrations: 12, 4, 1.2, 0.4, 0.12 and 0.04 μg/ml; final concentrations in the assay ranged, therefore, between 3 μg/ml and 0.1 μg/ml. Human interferon was diluted to give the following series of concentrations: 4000, 1200, 400, 120 and 40 IU/ml; final concentrations in the assay ranged, therefore between 1000 and 10 IU/ml. The infected cultures were incubated at 37° C. in a humidified atmosphere of 5% $CO_2$ in air until plaques were clearly visible (2-3 days for HSV-1; usually 1 day for HSV-2). The cultures were fixed in formal saline, the agarose overlays were carefully washed off, and then the cell monolayers were stained with carbol fushsin. A stereo microscope was used to count plaques. By reference to the number of plaques in virus control monolayers (untreated cultures) the percentage reduction in plaque count for each combination was calculated.

| Synergy between Compound A and human interferon against HSV-1 and HSV-2 in MRC-5 cells | | | |
|---|---|---|---|
| a. Activity against HSV-1 $IC_{50}$* (μg/ml) of A in presence of | | | |
| 0 | 10 | 30 | 100 IU/ml of human inteferon (IFN) |
| 0.34 | 0.04 | 0.02 | 0.01 (for IFNα; (Wellferon**) |
| 0.45 | 0.34 | 0.19 | 0.14 (for IFNβ; (Fiblaferon 5***) |
| 0.40 | 0.22 | 0.19 | 0.19 (for IFNγ; (Amgen Biologicals***) |
| b. Activity against HSV-2 $IC_{50}$* (μg/ml) of A in presence of | | | |
| 0 | 10 | 30 | 100 IU/ml of human inteferon (IFN) |
| 0.62 | 0.29 | 0.21 | 0.09 (for IFNα; (Wellferon***) |
| 0.64 | 0.62 | 0.39 | 0.41 (for IFNβ; (Fiblaferon 5***) |
| 0.44 | 0.34 | 0.29 | 0.27 (for IFNγ; (Amgen Biologicals***) |

*$IC_{50}$ is the concentration required to reduce the control (untreated) plaque count by 50%.
**IFNα tested at 100 IU/ml in the absence of compound A against HSV-1 reduced the plaque count relative to control by 18%.
***IFN tested at 100 IU/ml in the absence of compound A produced no effect on plaque count.

We claim:

1. A pharmaceutical composition for use in treating viral infections comprising an interferon and an antiviral effective amount of a compound of formula (A):

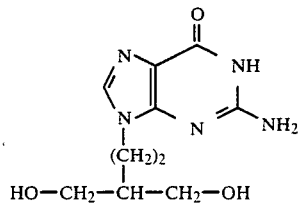

a pro-drug of the compound of formula (A) having the formula (B)

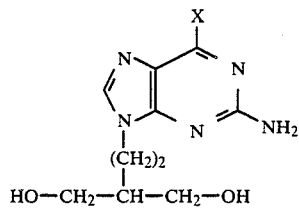

wherein X is hydrogen, or a pharmaceutically acceptable salt, a phosphate ester, or aryl derivative of either (A) or (B), and a pharmaceutically acceptable carrier.

2. A composition according to claim 1 comprising an interferon and the compound of formula (A) as defined in claim 1, or its sodium salt.

3. A composition according to claim 1 wherein the compound of formula (B) is that wherein X is hydrogen and wherein the two OH groups are in the form of acetyl derivatives.

4. A composition according to claim 1 wherein the interferon is prepared synthetically.

5. A composition according to claim 1 wherein the composition is formulated for topical application to the skin, and incorporates sodium lauryl sulphate as an additional ingredient.

6. A composition according to claim 1, wherein the composition contains 1000-200000 units of interferon per milligram of the compound of formula (A) or a pro-drug of formula (B) or a pharmaceutically acceptable salt or derivative of either (A) or (B).

7. A method of treatment of viral infections in a human or non-human animal, which comprises the administration to the animal of an effective, non-toxic amount of a combination of an interferon and a compound of formula (A) or a pro-drug of formula (B), or a salt or derivative of either (A) or (B), as defined in claim 1.

* * * * *